United States Patent
Eastman et al.

(10) Patent No.: US 9,848,802 B2
(45) Date of Patent: Dec. 26, 2017

(54) ACTIVITY TRACKING DEVICE AND ASSOCIATED DISPLAY

(71) Applicant: Under Armour, Inc., Baltimore, MD (US)

(72) Inventors: Kyle Maxell Eastman, Austin, TX (US); Clifford C. Drane, Jr., Austin, TX (US); William Wiley Fikes, Austin, TX (US)

(73) Assignee: Under Armour, Inc., Baltimore, MD (US)

( * ) Notice: Subject to any disclaimer, the term of this patent is extended or adjusted under 35 U.S.C. 154(b) by 93 days.

(21) Appl. No.: 14/634,328

(22) Filed: Feb. 27, 2015

(65) Prior Publication Data

US 2016/0249831 A1  Sep. 1, 2016

(51) Int. Cl.

| | |
|---|---|
| *G06T 11/20* | (2006.01) |
| *A61B 5/11* | (2006.01) |
| *G08C 17/02* | (2006.01) |
| *A61B 5/00* | (2006.01) |
| *A61B 5/024* | (2006.01) |
| *A61B 5/01* | (2006.01) |
| *H04Q 9/00* | (2006.01) |
| *A61B 5/0205* | (2006.01) |

(52) U.S. Cl.
CPC .............. *A61B 5/1118* (2013.01); *A61B 5/01* (2013.01); *A61B 5/024* (2013.01); *A61B 5/4809* (2013.01); *A61B 5/4815* (2013.01); *A61B 5/681* (2013.01); *G06T 11/206* (2013.01); *G08C 17/02* (2013.01); *H04Q 9/00* (2013.01); *A61B 5/02055* (2013.01); *A61B 5/742* (2013.01)

(58) Field of Classification Search
None
See application file for complete search history.

(56) References Cited

U.S. PATENT DOCUMENTS

| | | | |
|---|---|---|---|
| 2011/0230790 A1* | 9/2011 | Kozlov | A61B 5/4812 600/595 |
| 2014/0039842 A1* | 2/2014 | Yuen | A61B 5/6838 702/189 |
| 2016/0051184 A1* | 2/2016 | Wisbey | A61B 5/0205 600/301 |

OTHER PUBLICATIONS

Weber, Marc, Marc Alexa, and Wolfgang Müller. "Visualizing Time-Series on Spirals." Infovis. vol. 1. 2001.*
Presley (Polar Loop Review, "http://runprettyblog.com/wellthatsenlighteningrethinkyourdaypolarloopreview/", Dec. 31, 2013).*

(Continued)

*Primary Examiner* — Yu Chen
(74) *Attorney, Agent, or Firm* — Maginot, Moore & Beck LLP

(57) ABSTRACT

An activity tracking system includes a sensor device and a display device. The sensor device is configured to be carried by the user and includes at least one sensor configured to obtain the activity data for the user. The display device includes a display screen. The display device is configured to receive the activity data obtained by the sensor device and display the activity data about a circular axis on the display screen. The activity data includes sleep data on one side of the circular axis and awake data on an opposite side of the circular axis. The sleep data includes a start time and an end time for a daily retired sleep period, the end time occurring in a selected day and the start time occurring in a previous day.

16 Claims, 6 Drawing Sheets

(56) References Cited

OTHER PUBLICATIONS

Comstock (Apple watch, MobiHealthNews, "http://mobihealthnews.com/36396/longawaitedapplewatchtracksheartrateactivitycaloriesbutnotsleep", Sep. 9, 2014).*
Sporty Afros ("Keeping It Moving With the Polar Loop", http://sportyafros.com/all-about-alexandria/keeping-it-moving-with-the-polar-loop/, Dec. 6, 2013).*
Zhao, Jinfeng, Pip Forer, and Andrew S. Harvey. "Multi-Scale and Multi-Form Visualisation of Human Movement Patterns in the context of Space, Time and Activity: From Timeline to Ringmap.", GeoVisualization of Dynamics, Movement and Change Workshop, May 5, 2008.*
GeoVisualization of Dynamics, Movement and Change, 2008, supporting document for Zhao et al.*
"Track Your Sleep With LifeTrak Zone C410" [online], Dec. 2013 [retrieved on Feb. 27, 2015], Retrieved from the Internet: <URL: http://google.com/url?=http%3A%2F%2Fminimalistrunningshoes.org%2Ftrack-sleep-lifetrak-zone-c410&sa=D&sntz=1&usg=AFQjCNHBldKcFCgWeTwMvul04U5wOma-pA >.
"Polar Loop In-Depth Review" [online], Dec. 2013 [retrieved on Feb. 27, 2015], Retrieved from the Internet: <URL: http://dcrainmaker.com/2013/12/polar-depth-review.html >.

\* cited by examiner

ACTIVITY TRACKING DEVICE AND ASSOCIATED DISPLAY

FIELD

This document relates to the field activity tracking devices, and particularly to devices configured to collect and display motion, activity, and sleep information for a user.

BACKGROUND

Activity tracking devices are increasingly utilized by individuals interested in tracking metrics related to their personal health and fitness. These activity tracking devices include, for example, heart rate monitors, step counters, stair counters, GPS tracking devices, as well as various other motion and biometric tracking devices. The popularity and increasing use of activity trackers creating vast amounts of data coming from disparate sources over large periods of time. Because of the vast amounts of data collected over large periods of time, it is often difficult to present the data to the user in a logical easy-to-comprehend form.

Various display arrangements have been implemented in past devices which present data to the user in a summarized format. For example, some activity tracking devices have displayed activity data by providing a horizontal axis representing a twenty-four hour day. Sleep activity is represented with bars below the horizontal axis and awake activity is represented with bars above the horizontal axis. A transition from sleep to awake time is shown by a transition from below to above the horizontal axis. In another related display arrangement, the twenty-four hour axis is arranged in a circle, with a division of days at the top or bottom of the circle. Later times are usually expressed by points further along the circle in a clockwise direction. This arrangement provides the user with a more cyclical clock-like view of the day with activity or sleep data represented in an intuitive manner around the circular display.

While these exemplary methods have been useful in presenting daily exercise, activity, and sleep behavior in a summarized display, much information is omitted from these displays. For example, it is often difficult for the user to quickly and easily obtain view data from a previous day that may be relevant to the currently summarized day. It is also difficult for a user to transition quickly and easily between days. Accordingly, it would be advantageous to provide a display configured to show additional context data related to daily exercise, motion, and sleep behavior. It would also be advantageous if the user were able to quickly and easily obtain data collected over a number of previous days.

SUMMARY

In accordance with one exemplary embodiment of the disclosure, there is provided an activity tracking arrangement configured to provide activity data to a user. The activity tracking arrangement includes a sensor device and a display device. The sensor device is configured to be carried by the user and includes at least one sensor configured to obtain the activity data for the user. The display device includes a display screen. The display device is configured to receive the activity data obtained by the sensor device and display the activity data about a circular axis on the display screen. The activity data includes sleep data on one side of the circular axis and awake data on an opposite side of the circular axis. The sleep data includes a start time and an end time for a daily retired sleep period, the end time occurring in a selected day and the start time occurring in a previous day.

Pursuant to another exemplary embodiment of the disclosure, a computer readable medium contains instructions for controlling a display device by receiving activity data from a sensor device carried by the user. The computer readable medium also contains instructions for processing the activity data for use in association with a circular axis and displaying the activity data in association with the circular axis on a display screen. The activity data includes sleep data on one side of the circular axis and awake data on an opposite side of the circular axis. The sleep data includes a start time and an end time for a daily retired sleep period, with the end time occurring in a selected day and the start time occurring in a previous day.

In accordance with another exemplary embodiment of the disclosure, a method is disclosed for providing activity data to a user. The method includes receiving activity data from a sensor device carried by the user, and processing the activity data for use in association with a circular axis. The method further includes displaying the activity data on a display screen in association with the circular axis. The activity data includes sleep data on one side of the circular axis and awake data on an opposite side of the circular axis. The sleep data includes a start time and an end time for a daily retired sleep period, the end time occurring in a selected day and the start time occurring in a previous day.

Pursuant to yet another exemplary embodiment of the disclosure, there is provided an activity tracking arrangement configured to provide activity data to a user. The activity tracking arrangement includes a sensor device and a display device. The sensor device is configured to be carried by the user and includes at least one sensor configured to obtain the activity data for the user. The display device includes a display screen. The display device is configured to receive the activity data obtained by the sensor device and display the activity data about a circular axis on the display screen. The activity data includes sleep data on one side of the circular axis and awake data on an opposite side of the circular axis. The activity data includes an overlap region wherein sleep data and awake data are shown for a same period of time.

In accordance with yet another exemplary embodiment of the disclosure, there is provided a method of providing activity data to a user. The method comprises receiving activity data from a sensor device carried by the user and processing the activity data for use in association with a circular split axis display including a circular axis. The method further comprises displaying the activity data on the circular split axis display, the activity data including sleep data on one side of the circular axis and awake data on an opposite side of the circular axis, the activity data including an overlap region wherein sleep data and awake data is shown for the same period of time.

The above described features and advantages, as well as others, will become more readily apparent to those of ordinary skill in the art by reference to the following detailed description and accompanying drawings. While it would be desirable to provide an activity tracking device and associated display that provides one or more of these or other advantageous features, the teachings disclosed herein extend to those embodiments which fall within the scope of the appended claims, regardless of whether they accomplish one or more of the above-mentioned advantages.

DESCRIPTION

Figure 1:
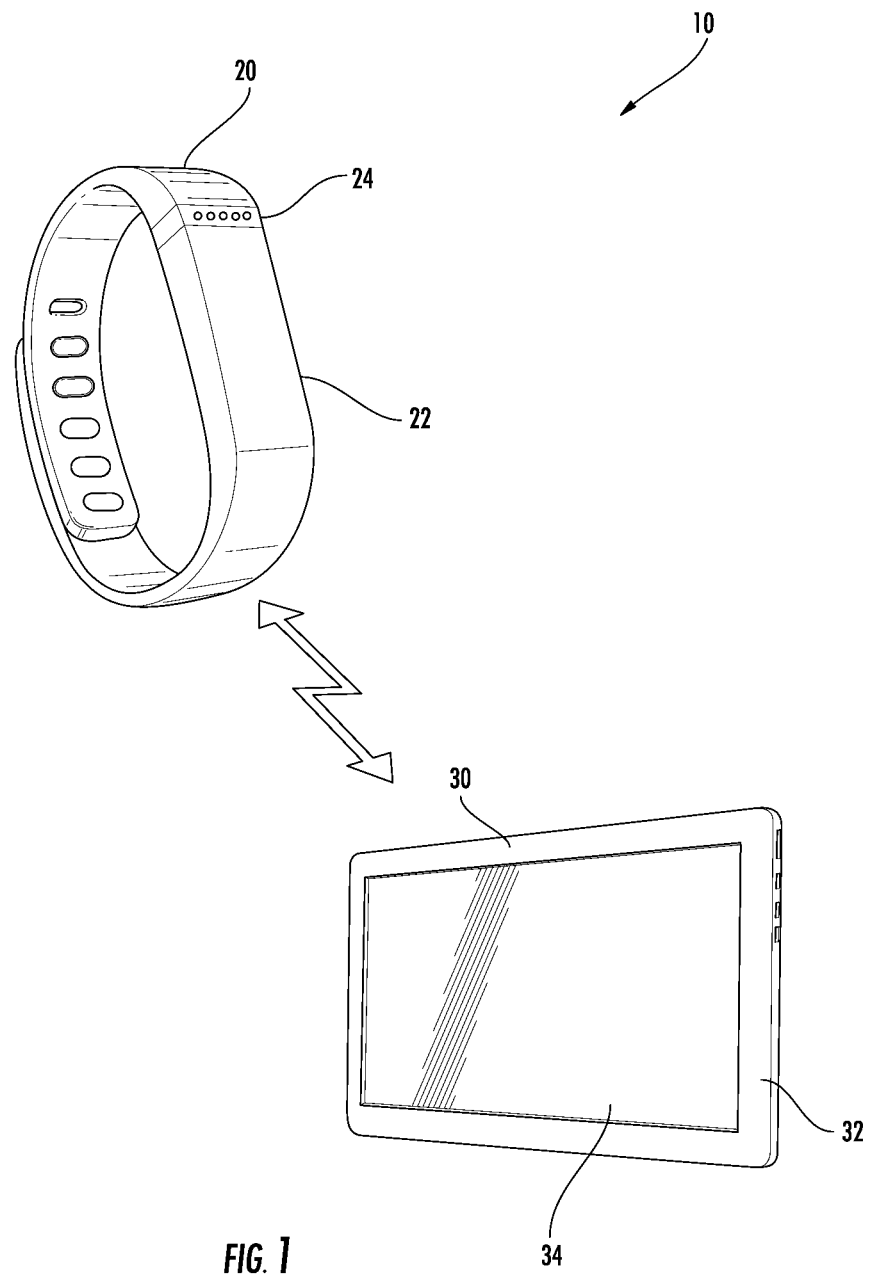
FIG. 1 shows an exemplary embodiment of an activity tracking system including a sensor device and a display device.
Figure 2:
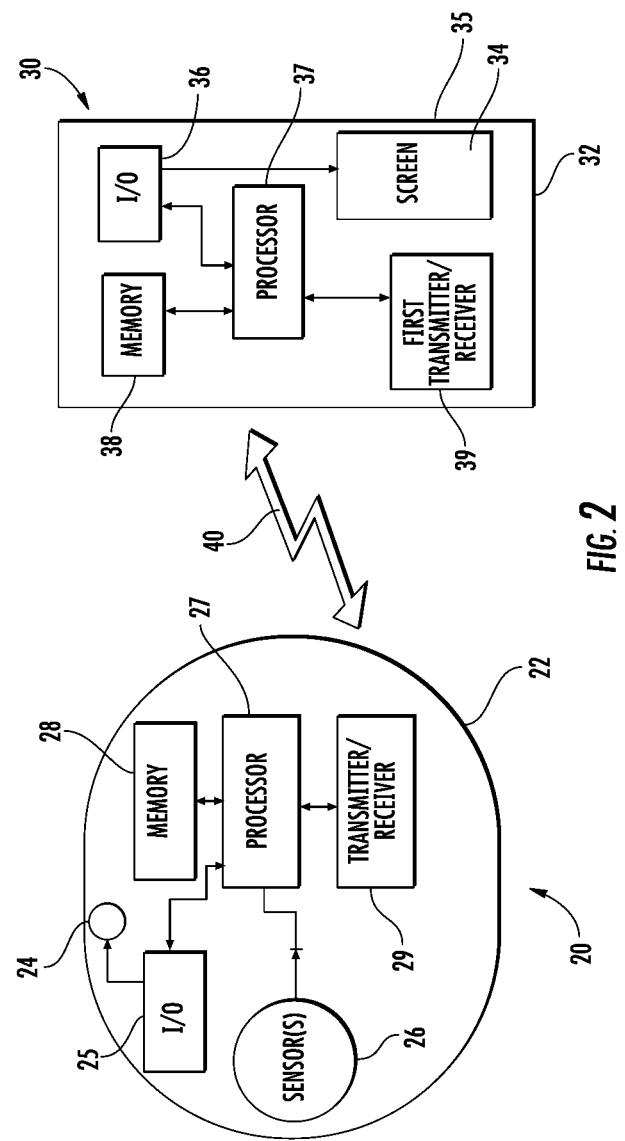
FIG. 2 shows electronic components in the sensor device and the display device of the activity tracking system of FIG. 1.

With reference to FIGS. 1-2, an exemplary embodiment of an activity tracking system 10 includes an activity sensor device 20 and an electronic display device 30. The activity sensor device 20 is designed and dimensioned to be worn on or carried by the body of a user and collect activity information about the user. The activity sensor device 20 is in communication with the electronic display device 30, and is configured to deliver the collected activity data about the user to the electronic display device 30. The electronic display device 30 is designed to process the activity data and display the collected information to the user in a format that shows context for daily exercise, general activity, and sleep behavior.

Sensor Device

The activity sensor device 20 (which may also be referred to herein as a "sensor device") may be provide in any of various forms and is configured to collect any of various types of activity data related to a user. Such activity data may be, in particular, human kinematic and/or physiological data that provides information about a level of activity during awake times and sleep quality during sleep times. For example, the sensor device 20 may be configured to collect one or more of step data, body motion data, distance traversal data, altitude data, heart rate data, body temperature data, breathing data, environmental/positional data (such that provided by a GPS receiver), or any of various other types of personal metrics that may be relevant to determining awake time activities or sleep quality of the user. Accordingly, the term "activity data" as used herein refers to data collected during a user's wake time or sleep time, and such data may indicate the user's participation in high intensity activity, sedentary activity, or various degrees of activity in-between. In at least one embodiment, the sensor device 20 may be an activity tracker configured to measure steps walked, stairs climbed, quality of sleep, as well as various other personal metrics (such "activity trackers" are commonly also referred to as "fitness trackers"). Examples of activity trackers include those sold under the trademarks FITBIT®, JAWBONE® and UNDER ARMOUR®.

The sensor device 20 is configured to be worn or carried by the human user. For example, in the embodiment shown in FIG. 1, the sensor device 20 is provided as a wrist band that the user straps to his or her wrist. However, it will be recognized that in other embodiments, the sensor device 20 may be provided in any of various different forms, such as a module that clips on to clothing or fits in a pocket of the user, a watch, a mobile phone or other personal electronics device. In the embodiment disclosed herein, the sensor device 20 is shown as being a completely separate unit from the display device 30. However, in at least one embodiment, the sensor device 20 and the display device 30 are provided as a single unit. For example, the sensor device 20 and the display device 30 may be combined on a mobile phone or other personal electronics device.

With continued reference to the embodiment of FIGS. 1 and 2, the sensor device 20 includes a protective outer shell or housing 22 designed to retain and protect various sensors and other electronic components positioned within the housing 22. The housing 22 may be provided in various forms. In at least one embodiment, the housing 22 includes a relatively rigid portion that securely retains the electronic components and a more resilient portion as an outer layer that provides shock absorption features in the event the sensor device 20 is dropped by the user.

The sensor device 20 may also include other features visible on the housing 22 such as an I/O interface 25, which may include a display 24, one or more connection ports (not shown), or other input and output hardware and software. The display 24 may vary based on the type of device. For example, in one embodiment the display 24 may simply be one or more lights configured to communicate information to the user (e.g., progress towards a goal). In another embodiment, the display 24 may be an LCD or LED screen that provides more specific information to the user (e.g., total number of steps for the day). The connection ports may be used to connect the sensor device 20 to a power source or to share data with other electronic devices.

As shown in FIG. 2, the sensor device 20 includes electronic circuitry comprising one or more sensors 26, a processor 27, a memory 28, and a transceiver 29. The sensor device 20 also includes a battery (not shown) configured to power the various electronics devices within the sensor device 20. In at least one embodiment, the battery of the sensor device 20 is a rechargeable battery. In this embodiment, the sensor device 20 may be placed in or connected to a battery charger configured for use with the sensor module in order to recharge the battery.

The sensors 26 may be provided any of various devices configured to collect the activity data, including step data, motion data, distance traversal data, altitude data, heart rate data, body temperature data, breathing data, environmental/positional data, or any of various other types of personal metrics that may be relevant to determining activities of the wearer. In at least one embodiment, the sensor is a 3-axis accelerometer configured to detect the steps of the wearer during walking and running, and general movements of the wearer during more sedentary periods such as sleep. Of course, it will be recognized by those of ordinary skill in the art that numerous other sensors may be used, depending on the type of activity the sensor device 20 is designed to detect.

With continued reference to FIG. 2, the processor 27 may be any of various microprocessors as will be recognized by those of ordinary skill in the art. The processor 27 is configured to receive signals related to receive activity data from the sensors 26 and process such signals. The processor 27 is connected to the memory 28 and the transceiver 29, and may deliver received activity data to one or both of the memory 28 and the transceiver 29. Additionally, the processor 27 may perform some processing on the received activity data prior to delivery to the memory 28 or transceiver 29. For example, the processor 27 may associate the received activity data with a particular time, day and/or event. The processor 27 is also connected to the I/O interface 25, and may send signals to the I/O interface 25 which results in illumination of the display 24.

The memory 28 is configured to store information, including activity data that may be retrieved, manipulated or stored by the processor 27, as well as software for execution by the processor 27. The memory 28 may be of any type capable of storing information accessible by the processor 27, such as a memory card, ROM, RAM, write-capable, read-only memories, or other computer-readable medium. The data may be stored in the memory 28 in a relational database as a table having a plurality of different fields and records, XML documents, or flat files. The data may also be formatted in any computer-readable format such as, but not limited to, binary values, ASCII or Unicode.

The transceiver 29 is an RF transmitter and receiver configured to transmit and receive communications signals over a short range using a wireless communications technology, such as Bluetooth®, using any of various communications protocols, such as TCP/IP. Such transceivers are well known and will be recognized by those of ordinary skill in the art. The transceiver 29 is particularly configured to communicate with the display device 30 when the sensor device 20 is within range of the display device 30, and transmit activity data to the display device.

Display Device

With continued reference to FIG. 2, in at least one embodiment, the display device 30 is a handheld computing device. In this embodiment, the display device 30 includes an input/output interface 36, a processor 37, a memory 38, and a transceiver 39. While a tablet computer has been shown as the display device 30 in FIGS. 1 and 2, it will be appreciated that the display device 30 may be provided in other forms in addition to or in lieu of the tablet computer. For example, the display device 30 may be a standalone device, such as a desktop PC or smart television. Alternatively, the display device may be another type of portable or handheld computing device such as a watch, smartphone, laptop computer, or any of various other mobile computing devices. As will be recognized by those of ordinary skill in the art, the components of the display device 30 may vary depending on the type of display device used. Such alternative display devices may include much of the same functionality and components as the display device 30 shown in FIGS. 1 and 2, but may not include all the same functionality or components.

The display device 30 includes a protective outer shell or housing 32 designed to retain and protects the electronic components positioned within the housing 32. The housing 32 may be provided in various forms. In at least one embodiment, the housing 32 includes a relatively rigid portion that securely retains the electronic components and a more resilient portion as an outer layer that provides shock absorption features in the event the sensor device 20 is dropped by the user.

With continued reference to FIG. 2, the I/O interface 36 of the display device 30 includes software and hardware configured to facilitate communications with the sensor device 20 carried by the user. The hardware includes a display screen 34 configured to visually display graphics, text and other data to the user. In particular, the display screen 34 of the I/O interface 36 is configured to display activity data received from the sensor device 20. The hardware also may also include a microphone and speakers to facilitate audio communications with the user. In at least one embodiment, the display screen 34 is a touch screen display that allows the user to see data presented on the display screen 34 and input data into the display device 30 via a keyboard on the touch screen.

The processor 37 of the display device 30 may be any of various processors as will be recognized by those of ordinary skill in the art. The processor 37 is connected to the I/O interface 36, the memory 38, and the transceiver 39, and is configured to deliver data to and receive data from each of these components. In at least one embodiment, the processor 37 is configured to process raw activity data received from the sensor device 20 and transform the activity data into a graphical format for presentation on the display screen 34.

The memory 38 is configured to store information, including data, software and firmware for execution by the processor 37. The data may be, in particular, activity data related to the activities of the user. The memory 38 may be of any type of device capable of storing information accessible by the processor, such as a memory card, ROM, RAM, write-capable, read-only memories, or other computer-readable medium as will be recognized by those of ordinary skill in the art.

The transceiver 39 is an RF transmitter and receiver configured to transmit and receive communications signals over a short range using a wireless communications technology, such as Bluetooth®, using any of various communications protocols, such as TCP/IP. Such transceivers are well known and will be recognized by those of ordinary skill in the art. The transceiver 39 is particularly configured to communicate with the transceiver 29 of the sensor device 20. The display device 30 also includes a battery (not shown) configured to power the transceiver 39 and various other the electronic components within the display device 30. In at least one embodiment, the transceiver 39 is configured to allow the display device 30 to communicate with a wireless telephony network, as will be recognized by those of ordinary skill in the art. The wireless telephony network may comprise any of several known or future network types. For example, the wireless telephony network may comprise commonly used cellular phone networks using CDMA or FDMA communications schemes. Some other examples of currently known wireless telephony networks include Wi-Fi, WiMax, GSM networks, as well as various other current or future wireless telecommunications arrangements.

Raw activity data collected by the sensor device 20 may be processed by the display device 30 or delivered to a remote server for further processing. The processing to be performed may depend on various factors including the type of data received and different subscriptions of the user/athlete. Typical processing might relate to the user's current activity level, trends, history, training state, etc. For example, the computer processing the raw data may calculate an activity level based on a combination of inputs, including, for example, steps taken over a period of time, heart rate, etc. In at least one embodiment, GPS data is used to determine various athletic data points, such as the speed of the athlete calculated over different time periods, total distance traveled, or the route taken by the athlete during a sporting event. Furthermore, the activity data may be processed into different forms and formats, depending on the particular device that will ultimately be used to view the processed data. For example, the activity data may be processed into a first format that will allow it to be viewed on a watch and into a second format that will allow it to be viewed on the monitor of a personal computer. While these are but a few examples of how the raw data may be processed, those of skill in the art will recognize that nearly countless other possibilities exist for how the data received from the sensor device 20 will be processed for subsequent viewing and analysis. After the raw activity data is transmitted and processed, the processed data may then be displayed or otherwise presented on a user interface of the display device 30.

In operation, when a user carries the sensor device 20, activity data is delivered to the display device 30 from the sensor device 20. As represented by arrow 40, in FIGS. 1 and 2, the sensor device 20 is configured to transmit a wireless RF signal representative of the activity data to at least one display device 30, such as the tablet. In addition, the activity data may also be transmitted to additional computing devices, such as a watch or a laptop computer where the activity data may be conveniently displayed for the user. In other embodiments, a wired connection may exist between the display device 30 and the sensor device 20, and the activity data may be transferred over the wired connection.

In at least one embodiment, this transmission from the sensor device 20 to the display device 30 occurs automatically without the user needing to prompt the transmission. Because the transmissions are automatic, some mechanism may be used to turn on the transceiver 29 of the sensor device 20 or otherwise indicate that automatic transmissions should begin. For example, in one embodiment, an on/off switch is provided on the sensor device 20 that allows the athlete to begin automatic transmissions of data from the sensor device 20. In another embodiment, the sensor device 20 may be configured to begin transmissions once it receives a confirmation that the display device 30 is within range of the sensor device 20. In other embodiments where communications between the sensor device 20 and the display device 30 are made with a wired connection, communications only occur when the wired connection is established between the sensor device 20 and the display device 30.

The activity data transmitted to the display device 30 is processed to determine one or more of various activity parameters. These activity parameters may simply include awake times or sleep times. However, in at least one embodiment, the activity parameters determine various additional parameters, such as an intensity level for an activity over a given period of time or a sleep quality over a period of time. For example, if the activity data indicates that the user is walking or running, the appropriate processor 27 or 37 may determine that the user is participating in a high intensity awake activity. On the other hand, if the activity data indicates that the user is sitting or generally sedentary, the appropriate processor 27 or 37 may determine that the user is participating in a lower level awake activity. If the user indicates on the sensor device 20 or on the display device 30 that he or she has retired to bed (e.g., by making an appropriate selection on the device 20 or 30), the appropriate processor 27 or 37 may determine a quality of sleep of the user by determining activity levels during sleep. Relatively low movement during sleep may indicate deeper sleep levels and significant movement during sleep may indicate lighter sleep or even additional awake times. When the user awakens the following morning, the appropriate processor 27 or 37 may automatically determine based on the activity signals that the user has awakened from his or her sleep and is participating in activities of various intensities.

Circular Split-Axis Display

Figure 3:
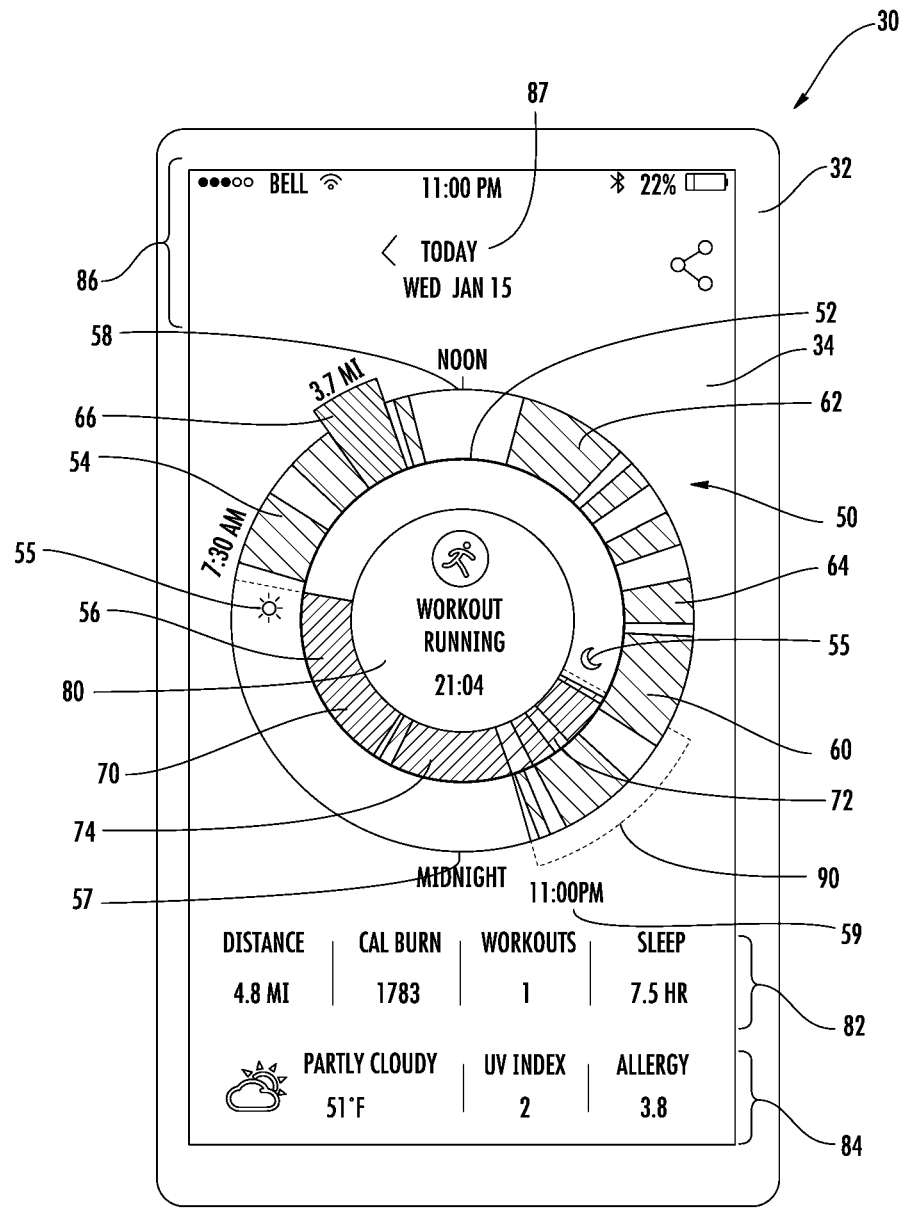
FIG. 3 shows a circular split axis display on the display device of FIG. 1.

With reference now to FIG. 3, the processor 37 is configured to communicate with the I/O interface 36 and display information about the user's awake activity and sleep activity on the display screen 34 of the display device 30. In FIG. 3, a summary of the user's activity data for a particular day is shown on the display screen 34 in the form of a circular split-axis display 50. The circular split axis display 50 includes a circular "axis" 52 that represents some period of time such as twelve hours or twenty-four hours. Periods of time are represented on the circular axis 52 in a clock-like manner. In the exemplary embodiment of FIG. 3, a twenty-four hour period of time is shown with midnight 57 at the bottom of the circular axis 52 (i.e., at the six-o'clock position) and noon 58 at the top of the circular axis 52 (i.e., at the twelve-o'clock position). Other times are spaced accordingly along the circular axis 52 (e.g., 6 pm at the three-o'clock position and 6 am at the nine o'clock position). A current time 59 may also be shown on the circular axis 52 to indicate to the user the current time of day. Additionally, indicia 55 for sunrise and sunset times on the displayed day (e.g., January 15 in FIG. 3) may be shown on the circular split axis display 50.

Awake time and sleep time activity is represented by a number of blocks positioned about the circular axis 52. Awake time activity is represented by a number of awake blocks 60 extending radially outward from the circular axis 52. Sleep time activity is represented by a number of sleep blocks 70 extending radially inward from the circular axis 52. No blocks are present at times on the circular axis 52 on the where the user was not carrying the sensor device 20 (e.g., the user was showering), the sensor device was powered off, or no readings were taken by the sensor device for another reason.

The awake blocks 60 and the sleep blocks 70 are provided by arc shapes (which may also be referred to herein as "frusto-pie shapes") of different colors. For example, the awake blocks 60 may be red in color, and the sleep blocks 70 may be blue in color. It will be recognized that in other embodiments, the awake blocks 60 and the sleep blocks 70 may be provided in any of various colors and shapes. The degree of the arc covered by each block 60 or 70 indicates the period of time covered by the block. For example, if the block covers 15° of the 360° circular axis 52 (i.e., $\frac{1}{24}^{th}$ of the circular axis), the block may be considered to cover a one hour period of time.

The plurality of awake blocks 60 that extend in a radially outward direction cover portions of an outer disc 54 extending around circular axis 52. The awake blocks 60 represent different activities or activity levels based on a variation in color or the extent of outward extension from the circular axis 52. For example, more sedentary activities with relatively little body movement, such as sitting at a desk, eating or watching television may be represented by a sedentary activity block having a lighter color (e.g., a relatively light red or pinkish block). Block 62 in FIG. 3 represents a sedentary activity block. More strenuous activities such as walking or cleaning the house may be represented by a moderate activity block having a darker color (e.g., a relatively dark red or crimson block). Block 64 in FIG. 3 represents a moderate activity block. High intensity aerobic activities, such as running, may be represented by high intensity blocks having a relatively dark color and extending radially outward past other activity blocks. Block 66 in FIG. 3 represents a high intensity activity block.

The plurality of sleep blocks 70 that extend in a radially inward direction cover portions of an inner disc 56 extending around circular axis 52. The sleep blocks 70 represent different sleep qualities based on a variation in color or the extent of inward extension from the circular axis 52. For example, periods of relatively light sleep involving significant body movement of the user may be represented by a light sleep block having a lighter color (e.g., a relatively light blue block). Block 72 in FIG. 3 represents a light sleep block. Periods of deeper sleep involving little body movement may be represented by a deep sleep block having a darker color (e.g., a relatively dark blue block). Block 74 in FIG. 3 represents a deep sleep block. The sleep blocks 70 typically cover sleep during a time when the user has retired to bed for the evening. However, in at least some embodiments, the sensor device 20 is configured to determine that a user is napping or otherwise sleeping even if the user does not indicate that he or she has retired for the evening for a primary sleep period.

As used herein, the term "daily retired sleep period" refers to a period of sleep that is intended to be the user's primary sleep period for a daily extended time that is relatively close to twenty four hours (e.g., between 16 and 30 hours), wherein the user intends to be awake for most of the daily extended time except for the primary sleep period. Each daily extended time includes the daily retired sleep period, awake time, and may also include one or more nap times. Awake time for each daily extended time may occur in the same calendar day in which the daily retired sleep period begins, or awake time may occur in the following calendar day after the day in which the daily retired sleep period begins. For example, if the daily retired sleep period begins at 10 pm on one day and ends at 6 am the following day, the awake time would occur the following day (e.g., starting at 6 am) after the start of the daily retired sleep period begins. On the other hand, if the daily retired sleep period begins at 1am, the upcoming awake time would occur in the same day (e.g., starting at 9 am). In yet another example, if the daily retired sleep period begins at 8 am, the awake time may occur the same day and extend into the following day (e.g., from 4 pm one day to 8am the following day). While the user intends to be awake for most of the daily extended time, one or more naps with sleep time might also occur during the daily extended time in addition to the daily retired sleep time. Accordingly, it will be recognized that a nap or other relatively short period of sleep is not part of the "daily retired sleep period". Also, based on the foregoing examples, it will be recognized that the "daily retired sleep period" may extend over times falling within one calendar day (e.g., from 1am to 9 am on one day) or two calendar days (e.g., from 11 pm one day to 7 am the following day).

A determination that a daily retired sleep period is occurring or has occurred may be determined in any of various ways. For example, a daily retired sleep period may begin when a user indicates that he or she intends to retire for the day (e.g., by making an appropriate selection on the sensor device 20 or the display device). As another example, the daily retired sleep period may be a detected period of sleep time that is greater than a predetermined period (e.g., greater than three hours), and is therefore not considered to be merely a nap. The term "nighttime sleep" as used herein refers to a daily retired sleep period that begins at a time that is near or after sunset but is prior to sunrise.

In the embodiment described herein, the circular split axis display 50 covers a full twenty-four hour period of time for the current day (i.e., midnight to midnight). At the same time, the circular split axis display shows full period of nighttime sleep that started the previous evening (i.e., prior to midnight on the current day). Accordingly, when the user enters nighttime sleep on one day at a later time than on a previous day, more than twenty-four hours of time will be represented on the circular split axis display 50. As a result, an overlap region 90 will be shown on the display. Within this overlap region 90, awake blocks 60 and a sleep blocks 70 are shown covering the same period of time. For example, in the embodiment of FIG. 3, the overlap period covers a region starting at about 8 pm on a previous day up to the current time of day (i.e., 11 pm). In this example, the user retired for evening sleep on the previous evening (i.e., January 14) about 8 pm—just after sunset, and slept until about 7 am the current day (i.e., January 15)—just after sunrise. The user's sleep data was logged in blocks 70 on the inner disc 56 of the circular split axis display 50. Thereafter, activity data for the current day was logged for the user, and this activity data was displayed in blocks 60 on the outer disc 54 of the circular split axis display 50. The user remained awake on the evening of the current day (i.e., January 15) until a time after he retired the previous evening. In particular, the current time shown on the current day is 11 pm, and the user remains awake. Accordingly, the overlap region 90 includes sleep blocks 70 in the inner disc 56 (for sleep periods) as well as awake blocks 60 on the outer disc 54 (for awake periods). The circular split axis display 50 will continue to log activity data for the given day (and even into the following day) until the user retires for the day and begins a new daily retired sleep period.

With continued reference to FIG. 3, if the user remains awake after 11:59 pm on the current day (i.e., until after midnight on January 15), the overlap region 90 will continue to extend as activity data continues to be logged for the user on the outer disc 54. However, the extent of the overlap region 90 in the example of FIG. 3 is limited to the start of the activity period for the day being displayed (i.e., January 15). In other words, if the user remains awake and active for a twenty-four hour period of time without sleep, the system 10 will end activity logging at the end of twenty-four consecutive hours of awake time. The system 10 will then generate a new circular split axis display for the new day (i.e., January 16), starting with activities that occurred after midnight on the new day.

As described above in the example of FIG. 3, the circular split axis display 50 is configured to display a different period of time, depending on the times the user begins each daily retired sleep period. Typically, the period of time covered by the circular split axis display 50 extends from a time one day when a user retires for nighttime sleep until a time on a following day when the user again retires for nighttime sleep. This period of time extending from a first start time of nighttime sleep until a second start time of nighttime sleep may extend for more than or less than twenty-four hours and may extend over one, two or even three days. As a first example, consider a user who retires for nighttime sleep after midnight on one day (e.g., 1am), and retires for nighttime sleep before midnight on the same day (e.g., 11 pm). In this case, the period of time covered by the circular split axis display 50 will be less than twenty-four hours (i.e., twenty-two hours extending from 1 am until 11 pm) and extend over only a single day (e.g., the circular axis 52 may extend from 1am until 11 pm on a single day).

As a second example, consider a user who retires for nighttime sleep before midnight on one day, and retires for nighttime sleep before midnight on the following day. In this case, the period of time covered by the circular split axis display 50 would extend over two days, but the total period of time covered may be more or less than twenty-four hours. If the user retired for nighttime sleep at an earlier time on the previous day and a later time on the following day (similar to the example of FIG. 3 where the user retires at 11 pm), the total period of time covered by the circular split axis display 50 will be more than twenty-four hours (e.g., about twenty-seven hours in the example of FIG. 3) and will include an overlap region 90. On the other hand, if the user retired for nighttime sleep at later time on the previous day and an earlier time on the following day (e.g., at 11 pm on the previous day and at 10 pm on the current day), the total period of time covered by the circular split axis display 50 will be less than twenty-four hours and will not include an overlap region 90.

As a third example, consider a user who retires for nighttime sleep before midnight on one day, and retires for nighttime sleep after midnight on the following day. In this case, the period of time covered by the circular split axis display 50 would extend over three days, and the total period of time covered will be more than twenty-four hours. Therefore, if the user retired for nighttime sleep at 11 pm on one day (e.g., January 14), stayed up until midnight on the following day (e.g., January 15), and then retired after midnight on the next day (e.g., at 1am on January 16), the total period of time covered by the circular split axis display 50 will be twenty-six hours and will extend over three days (January 14-16). In this case, the circular split axis display will include a two-hour overlap region 90 (between 11 pm on January 14 and 1am on January 16).

As shown in the preceding examples, it will be recognized that although the circular axis 52 extends over a twenty-four hour time period, the circular split axis display 50 may cover a period of time that is more than or less than twenty-four hours. Variations on the above examples are also contemplated. For example, in at least one embodiment, the circular split axis display 50 always covers a period of time of at least twenty-four hours. In this exemplary embodiment, the period covered by the circular split axis display 50 may start from either (i) the start of nighttime sleep prior to midnight on a previous day, or (ii) awake activity that started after midnight on the current day, which is then followed by a daily retired sleep period. Also, the period covered by the circular split axis display may end with one of (i) the start of nighttime sleep on the current day (provided it is after the start of nighttime sleep on the previous day such that the circular split axis display covers more than twenty-four hours), (ii) sleep or awake activity up to midnight at the start of the following day, or (iii) the start of another daily retired sleep period after midnight on the following day. Accordingly, although only a few limited embodiments of time periods covered by the circular split axis display 50 are shown herein, it will be recognized that numerous additional embodiments are possible.

In at least some embodiments, including one or more embodiments described above, a circular split axis display 50 displaying sleep and awake activity begins from the start of nighttime sleep on one day until the start of nighttime sleep on a following day. However, it is contemplated that in at least some embodiments, users may configure the circular nighttime display to begin or end upon the start of any of various times or events (e.g., the start of a daily retired sleep period between 6 am and noon on any given day), as desired by the user in order to show the most relevant activity information for a given day. This may be particularly advantageous for users working night-shift hours and typically sleep during daytime hours.

With continued reference to FIG. 3, in addition to the awake blocks 60 and the sleep blocks 70, the circular split axis display 50 includes additional data that is presented to the user. In the embodiment of FIG. 3, the circular split axis display 50 includes a center disc 80 configured to show any of various activity parameters. For example, the center disc 80 may show the current activity detected by the activity tracking system 10. Alternatively, in at least one embodiment, the center disc 80 may show activity for one of a selected blocks 60 or 70 on the circular split axis display 50. For example when the user touches one of the activity blocks (e.g., high intensity block 66) information related to this block may be presented on the center disc 80. This information may include any of various parameters, such as type of activity detected, activity time, heart rate, or any of various other parameters that may have been detected by the system 10 and is associated with the selected block.

In addition to the circular split axis display 50, additional information may also be provided on the display screen 34. For example, as shown in the embodiment of FIG. 3, the user is presented with a numerical summary of the day in a first lower portion 82 of the display screen 34. This first lower portion 82 includes the total distance traversed by the user for the day, the total calories burned, the number of detected "workouts" (e.g., high intensity periods) and the total hours of sleep for the user on the circular split axis display 50. A second lower portion 84 of the display screen 34 may be configured to provide other information such as weather information, news, messaging, or other selected information. Similarly, one or more upper portions 86 of the display screen 34 may be used to provide additional information, such as service provider logo, a date selector 87 for which activity data is displayed (which may be a current day or a previous day), or various menus for accessing additional data or functionality using the system 10.

Touch Scrolling for Circular Split Axis Display

Figure 4:
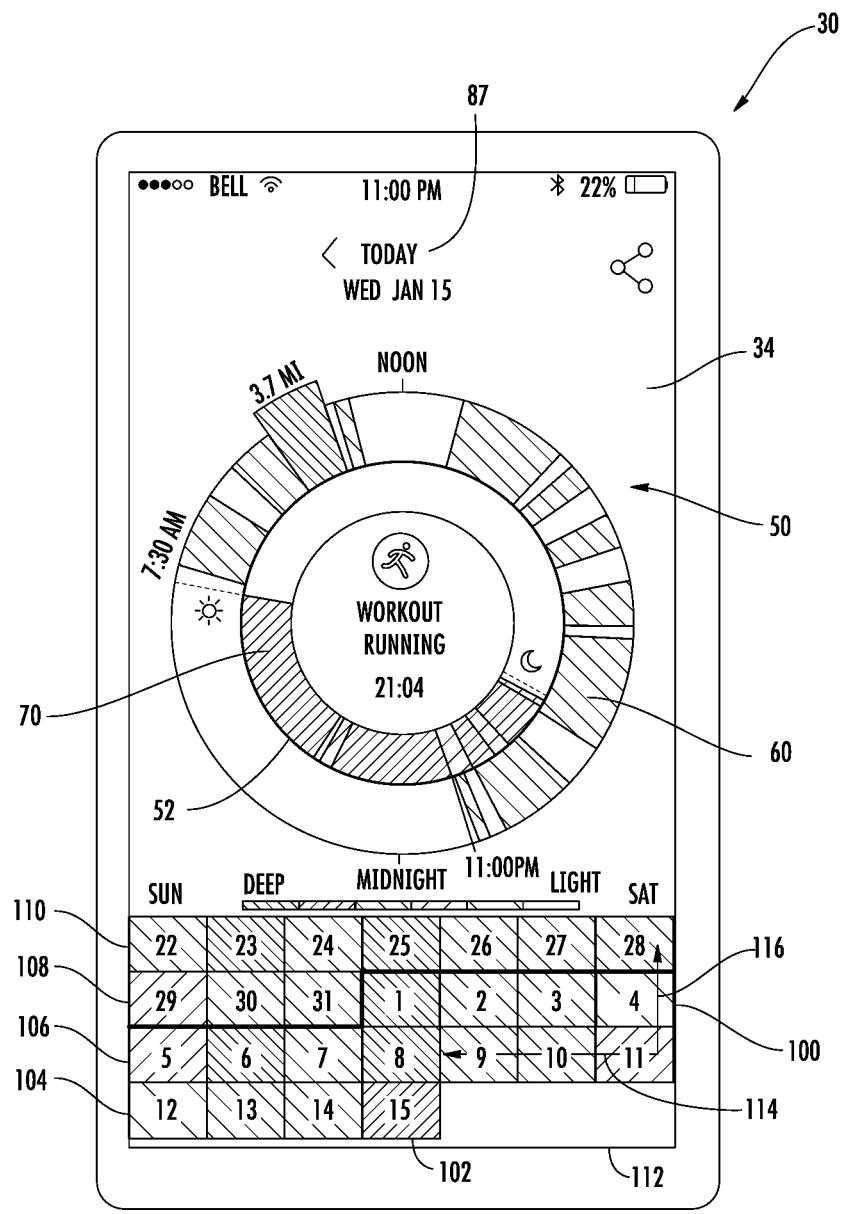
FIG. 4 shows an alternative embodiment of the circular split axis display of FIG. 3.

With reference not to FIG. 4, the user may be presented with a menu or shortcut that allows the user to pull up a multi-day table in the form of a calendar 100 on the display screen 34. For example, if the user swipes upward from the bottom perimeter of the screen, the calendar 100 may be presented across the bottom of the display screen 34, as shown in FIG. 4, in place of the first lower portion 82 and the second lower portion 84.

The calendar 100 displays a number of days in traditional calendar form with blocks representing each day, seven days in a row to show a given week, and several weeks stacked together. Accordingly, each vertical column of days will be for the same day of the week, (e.g., Sunday, Monday, Tuesday, etc.). The weeks presented on the calendar 100 may cover a single month (e.g., January 1-31), or may cover portions of multiple months (e.g., five weeks from January 25-February 21). In at least one embodiment, the number of weeks covered is a predetermined number of weeks (e.g., 4 weeks), including a week with a selected day and a number of immediately preceding weeks. For example, in FIG. 4, four weeks are displayed, including the week 104 with the selected date 102 (i.e., January 15), and the three immediately preceding weeks 106, 108 and 110 (i.e., the weeks starting December 22, December 29, and February 5). The days in the week that have yet to occur are represented by a void area 112 on the calendar 100.

If the user selects a different day in the date selector 87 in the upper portion 86 of the screen, the calendar 100 will refresh to include the selected date as well as earlier and/or later weeks, depending on the settings for the calendar. The selected date 102 is highlighted on the calendar 100. The user may also choose to select a different date by simply tapping on a different date on the calendar 100. When the user selects a different date, the circular split axis display 50 is refreshed to show the activity data for the selected date.

The calendar 100 in combination with the touch screen allows the user to quickly and easily review activity data for multiple days. In particular, the user may take his or her finger and scroll across different days of the calendar (i.e., by the user moving his or her finger in a left, right, upward or downward direction) and quickly view data for adjacent days on the calendar. In particular, as the user touches each day on the calendar 100, the circular split axis display 50 is refreshed, allowing the user to quickly compare one day to an immediately adjacent day on the calendar. For example, as shown by reference arrow 114, if the user begins on January 11, and scrolls horizontally toward the beginning of the week, the user is presented with a quick view of each day of the week on the circular split axis display 50. This may be particularly valuable to the user if the user wishes to quickly determine in which days of the week the user had the most sleep or in which days of the week the user had the most intense workouts. Because of the varying parameters of the activity data, including contrasting colors, positions, block sizes, this information may be easily viewed even if the user moves his or her finger across the screen relatively quickly. For example, if a user is trying to determine the amount and quality of sleep for the given week, a day where the user obtained little sleep or sleep quality was poor may be quickly determined based on the contrast of the sleep blocks for this day versus other days of the week. As another example, a user may realize a trend toward a later bedtime by simply scrolling a thumb or finger horizontally across a number of days and weeks.

In addition to quickly obtaining data for a given week, the user may also quickly obtain data about a particular day of the week across consecutive weeks. For example, as shown by reference arrow 116 in FIG. 4, if the user begins on January 11, and scrolls vertically upward, the user is presented with a quick view of activity data for each of several consecutive Saturdays. Again, this may be particularly valuable to the user if the user wishes to quickly determine typical activity data for the day in question. For example, the user may realize that his or her Saturdays tend to be more sedentary than realized, and may decide to schedule workouts for future Saturdays. Alternatively, the user may realize that he or she is in a pattern of little sleep on this day of the week, and may determine to get more sleep on this day in the future. As another example, the user may realize that he or she is in a trend of low sleep quality for a given day, and this may offer clues about how to improve sleep quality in the future (e.g., the user may be experiencing poor sleep quality every Thursday and may determine that the reason for this is due to a company happy hour or failure to exercise on Thursdays).

In addition to scrolling for data trends, the calendar also allows the user to view trends for the entire period shown on the calendar. In particular, if the user selects a particular statistic on the circular split axis display, such as sleep level, the calendar is converted to a grid that shows the last few weeks of that statistic in a color-coded format. The color coded format allows the user to view variations for the statistic across multiple weeks. For example, if the user selects an overall sleep quality for display on the calendar, the user may note a trend in the colors, such as darker colors during the weekend or lighter colors during the weekdays. This may provide the user with strategies to improve on weekday performance by taking actions that will result better sleep quality during the week. For example, the user may decide to walk after dinner on weekdays, read before bedtime, or plan for an earlier bedtime.

Helical Split Axis Display

Figure 5:
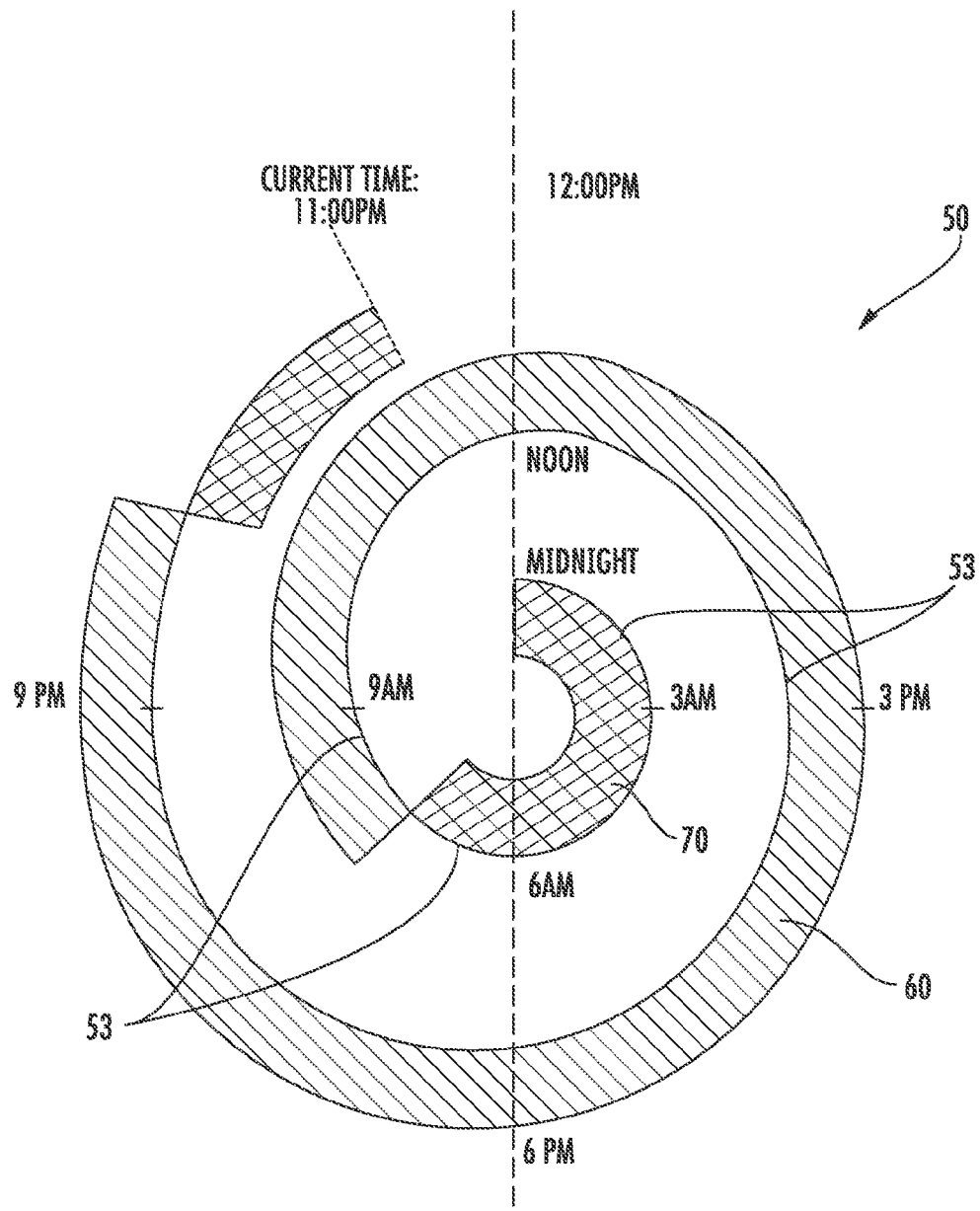
FIG. 5 shows a helical split axis display on the display device of FIG. 1.

While the examples of FIGS. 3 and 4 show the circular axis 52 as a circle, it will be recognized that in other embodiments the circular axis may be different types of circular axes but not perfect circles. For example, in at least one embodiment, the circular axis 52 may be oval-shaped. In another embodiment as shown in FIG. 5, the circular axis is helical or spiral shaped axis 53. The spiral axis 53 provides for a display that more closely follows the twelve hour clock concept, with each loop on the axis representing a twelve hour period of time. This allows the display 50 to include an entire day (i.e., twenty-four hours) of data with the spiral axis 53 making two complete revolutions to represent two twelve hour periods. In this manner, the spiral axis 53 presents a more canonical, clock-like time positions to which users are accustomed. For example, as shown in FIG. 5, the Gam and 6 pm times are both shown at the typical six-o'clock position along the axis 53. Whereas in FIG. 3, the Gam position is at the traditional nine-o'clock position, and the 3 pm position is at the traditional three-o'clock position. Similarly, the 9 am and 9 pm times are both shown at the typical nine-o'clock position on the axis. Awake blocks 60 are positioned on a radially outward side of the spiral axis 53 and sleep blocks 70 are positioned on a radially inward side of the spiral axis.

Figure 6:
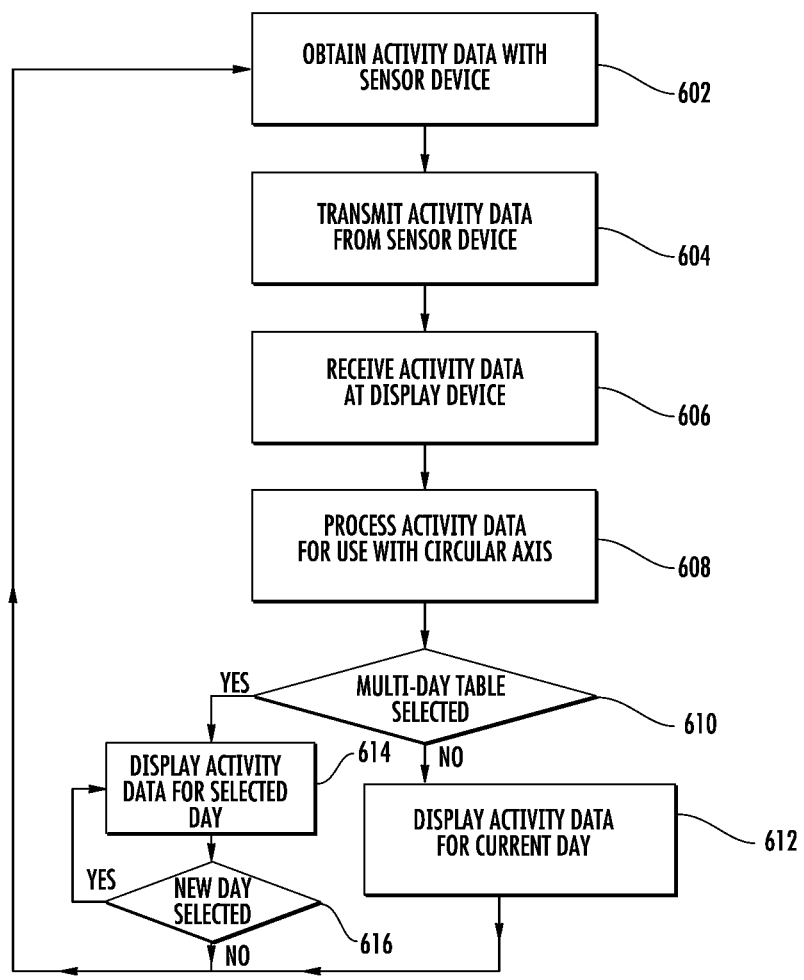
FIG. 6 shows a method for providing activity data to a user using the activity tracking system of FIG. 1.

With reference now to FIG. 6, a flowchart illustrates various steps of an exemplary method for providing activity data to a user. As shown in block 602 of the flowchart, the method includes obtaining activity data at a sensor device carried by a user. The activity data is then transmitted from the sensor device in block 604. As shown in block 606, the method further includes receiving the activity data at a display device. Then, in block 608, the activity data is processed at the display device for use in association with a circular axis that extends over a twenty-four hour period of time.

In block 610 a determination is made concerning the existing display on the display screen (i.e., whether the user has selected the multi-day table for display on the screen). If the multi-day table has not been selected, the method continues at block 612 and activity data for the current day is provided in association with the circular axis on the display screen of the display device. The activity data displayed in association with the on the display screen includes sleep data on an inner side of the circular axis and awake data on an outer side of the circular axis. The sleep data includes a start time and an end time for a daily retired sleep period, the end time occurring in a selected day and the start time occurring in a previous day. As described previously, the awake data is configured to overlap the sleep data on the circular axis to show a time when the user remained awake during the selected day that is later than the start time of the daily retired sleep period from the previous day.

With continued reference to FIG. 6, if the multi-day table has been selected at step 610, the method continues at block 614 with a determination of whether the multi-day table should be provided. If the multi-day table has been selected, the activity data for the selected day on the multi-day table is provided on the display screen in step 614. After some short period of time (e.g., 200 ms), the method continues at block 616 and a determination is made whether the user has selected a new day on the multi-day table (e.g., by scrolling his or her finger to an adjacent day to the previously selected day on the table). If the user has already selected a new day for display, the activity data for the selected new day is shown on the display screen. During this transition, the circular axis remains on the display screen and the activity data displayed about the circular axis changes from one selected day to the next. On the other hand, if a new day has yet to be selected, the activity data for the currently selected day remains on the display screen, the method returns to block 602 and the process is repeated.

The foregoing method may be accomplished with the assistance of a computer program stored in the memory 38 and executed by the processor 37 of the display device. The above described system and method solves a technological problem common in industry practice related to effective and efficient presentation of activity data to a user. Moreover, the above-described system and method improves the functioning of the computer/device by allowing activity data to be effectively communicated on a single display screen. The system and method also allows the user to easily view data over several days of logged data without changing the basic configuration of the display screen.

The foregoing detailed description of one or more exemplary embodiments of the activity tracking device and associated display has been presented herein by way of example only and not limitation. It will be recognized that there are advantages to certain individual features and functions described herein that may be obtained without incorporating other features and functions described herein. Moreover, it will be recognized that various alternatives, modifications, variations, or improvements of the above-disclosed exemplary embodiments and other features and functions, or alternatives thereof, may be desirably combined into many other different embodiments, systems or applications. Presently unforeseen or unanticipated alternatives, modifications, variations, or improvements therein may be subsequently made by those skilled in the art which are also intended to be encompassed by the appended claims. Therefore, the spirit and scope of any appended claims should not be limited to the description of the exemplary embodiments contained herein.

What is claimed is:

1. An activity tracking system configured to provide activity data to a user, the activity tracking system comprising:
a sensor device configured to be carried by the user, the sensor device including at least one sensor configured to obtain the activity data for the user; and
a display device including a display screen, the display device configured to receive the activity data obtained by the sensor device and display the activity data about only one closed loop circular axis on the display screen, the activity data including sleep data on one side of the only one closed loop circular axis and awake data on an opposite side of the only one closed loop circular axis, the sleep data including a start time and an end time for a daily retired sleep period, the end time occurring in a selected day and the start time occurring in a previous day, the awake data configured to overlap the sleep data on the only one closed loop circular axis when the user remained awake at a time during the selected day that is later than the start time of the daily retired sleep period from the previous day such that both the awake data and the sleep data are associated with at least one point on the only one closed loop circular axis.

2. The activity tracking system of claim 1 wherein the only one closed loop circular axis extends over a twenty-four hour time period.

3. The activity tracking system of claim 1 wherein sleep data is displayed on an inner side of the only one closed loop circular axis and awake data is displayed on an outer side of the only one closed loop circular axis.

4. The activity tracking system of claim 1 further comprising a multi-day table provided on the display screen, wherein activity data for different days is displayed on the only one closed loop circular axis on the display screen when the user scrolls across the multi-day table.

5. The activity tracking system of claim 4 wherein the multi-day table is provided in a calendar format.

6. The activity tracking system of claim 4 wherein the only one closed loop circular axis remains on the screen and the activity data displayed about the only one closed loop circular axis changes when the user scrolls across the multi-day table based on a selected day of the multi-day table.

7. A non-transitory computer readable medium containing instructions for controlling a display device by:
receiving activity data from a sensor device;
processing the activity data for use in association with a-only one closed loop circular axis extending over a 24 hour time period;
displaying a first arc in association with the only one closed loop circular axis, the first arc configured to display activity data therein;
displaying a second arc in association with the only one closed loop circular axis, the second arc such that at least a portion thereof is concentric to the first arc;
wherein a circumference of a circle which would be formed by the first arc is representative of awake data for a current 24 hour period;
wherein a portion of a circumference of a circle which would be formed by the second arc is representative of a previous 24 hour period in which a sleep activity began, and a remaining portion of the circumference of the circle which would be formed by the second arc is representative of the current 24 hour period; and
wherein the second arc is configured to represent the sleep activity which began in the previous 24 hour period and continued into the current 24 hour period, the second arc configured to overlap the first arc at one or more points on the closed loop circular axis such that both the awake data and the sleep data are associated with the one or more points on the only one closed loop circular axis.

8. The computer readable medium of claim 7 wherein the sleep data is displayed on an inner side of the only one closed loop circular axis and awake data is displayed on an outer side of the only one closed loop circular axis.

9. The computer readable medium of claim 7 further comprising providing a multi-day table on the display screen, receiving selections for different days as a user scrolls across the multi-day table, and displaying activity data for different days on the display screen when the user scrolls across the multi-day table.

10. The computer readable medium of claim 9 wherein the multi-day table is provided in a calendar format.

11. The computer readable medium of claim 9 wherein the only one closed loop circular axis remains on the screen and the activity data displayed about the only one closed loop circular axis changes when the user scrolls across the multi-day table.

12. A method of providing activity data to a user, the method comprising:
receiving activity data from a sensor device carried by a user;
processing the activity data for use in association with a closed loop circular axis;
displaying the activity data in association with the closed loop circular axis on a first portion of a display screen, the closed loop circular axis being the only closed loop circular axis displayed on the display screen, the activity data including sleep data on one side of the closed loop circular axis and awake data on an opposite side of the closed loop circular axis, the sleep data including a start time and an end time for a daily retired sleep period, the end time occurring in a selected day and the start time occurring in a previous day, the awake data configured to overlap the sleep data on the closed loop circular axis when the user remained awake at a time during the selected day that is later than the start time of the daily retired sleep period from the previous day; and displaying on a second portion of the display screen a calendar, the calendar providing for each day of a displayed month an indicator of at least one aspect of the sleep data.

13. The method of claim 12 wherein the closed loop circular axis extends over a twenty-four hour time period.

14. The method of claim 12 wherein sleep data is displayed on an inner side of the closed loop circular axis and awake data is displayed on an outer side of the closed loop circular axis.

15. The method of claim 12 further comprising receiving selections for different days as a user scrolls across the calendar, and displaying activity data for different days on the display screen when the user scrolls across the calendar.

16. The method of claim 15 wherein the circular axis remains on the screen and the activity data displayed about the circular axis changes when the user scrolls across the calendar.

* * * * *